(12) United States Patent
Karp et al.

(10) Patent No.: US 6,935,772 B2
(45) Date of Patent: Aug. 30, 2005

(54) FLUIDIC MIXER IN MICROFLUIDIC SYSTEM

(75) Inventors: Christoph D. Karp, Pasadena, CA (US); Stephen D. O'Connor, Pasadena, CA (US); Paren P. Patel, Sierra Madre, CA (US)

(73) Assignee: Nanostream, Inc., Pasadena, CA (US)

( * ) Notice: Subject to any disclaimer, the term of this patent is extended or adjusted under 35 U.S.C. 154(b) by 246 days.

(21) Appl. No.: 10/444,041

(22) Filed: May 21, 2003

(65) Prior Publication Data

US 2003/0198130 A1 Oct. 23, 2003

Related U.S. Application Data

(63) Continuation-in-part of application No. 09/632,681, filed on Aug. 7, 2000, now abandoned.

(51) Int. Cl.[7] .............................. B01F 13/00; G05B 7/00
(52) U.S. Cl. ....................... 366/341; 137/833; 137/827; 137/550; 422/101; 422/103
(58) Field of Search ................................. 366/341, 340; 137/833, 827, 550; 422/101, 103; 210/321.75, 321.84

(56) References Cited

U.S. PATENT DOCUMENTS

| | | | |
|---|---|---|---|
| 4,946,795 A | 8/1990 | Gibbons et al. ............. | 436/179 |
| 5,070,606 A | 12/1991 | Hoopman et al. ....... | 29/890.33 |
| 5,194,133 A | 3/1993 | Clark et al. ................. | 204/658 |
| 5,222,808 A | 6/1993 | Sugarman et al. .......... | 366/274 |
| 5,230,866 A | 7/1993 | Shartle et al. ............... | 422/103 |
| 5,376,252 A | 12/1994 | Ekstrom et al. ............ | 204/603 |
| 5,385,709 A | 1/1995 | Wise et al. ................... | 422/98 |
| 5,443,890 A | 8/1995 | Ohman ........................ | 428/167 |
| 5,534,328 A | 7/1996 | Ashmead et al. ............ | 428/166 |
| 5,545,367 A | 8/1996 | Bae et al. .................... | 264/401 |

(Continued)

FOREIGN PATENT DOCUMENTS

| | | | |
|---|---|---|---|
| EP | 0 107 631 | 5/1984 | .......... G01N/35/08 |
| EP | 0 933 126 | 8/1999 | ............ B01J/19/28 |
| EP | 1 123 734 A2 | 8/2001 | |
| WO | WO 97/00125 | 1/1997 | ............. B01F/5/06 |
| WO | WO 97/12665 | 4/1997 | ............. B01F/5/00 |
| WO | WO 98/45693 | 10/1998 | .......... G01N/27/26 |
| WO | WO 98/56505 | 12/1998 | ............. B01L/3/00 |
| WO | WO 99/17093 | 4/1999 | ............ G01N/1/10 |
| WO | WO 99/19717 | 4/1999 | .......... G01N/25/22 |
| WO | WO 99/29497 | 6/1999 | ............. B32B/3/00 |
| WO | WO 99/60397 | 11/1999 | ......... G01N/33/483 |
| WO | WO 00/21659 | 4/2000 | |
| WO | WO 00/22436 | 4/2000 | ......... G01N/33/567 |
| WO | WO 01/28670 | 4/2001 | ............. B01F/5/02 |
| WO | WO 02/10732 | 2/2002 | .......... G01N/27/26 |

OTHER PUBLICATIONS

Groisman et al., *Microfluidic Memory and Control Devices*, "Science Magazine," vol. 300, May 9, 2003, pp. 955–958.
Stroock, Abraham D., et al., *Chaotic Mixer for Microchannels*, "Science Magazine," vol. 295, Jan. 25, 2002, The American Association for the Advancement of Science, Stanford University's HighWire Press, pp. 647–651.

(Continued)

*Primary Examiner*—W. L. Walker
*Assistant Examiner*—Krishnan S Menon
(74) *Attorney, Agent, or Firm*—Vincent K. Gustafson

(57) ABSTRACT

Microfluidic devices capable of efficiently mixing two or more fluid are provided. Two or more microfluidic inlet channels defined in different sheets of material meet at an overlap region in fluid communication with an outlet channel. The channels are defined through the entire thickness of stencil sheets. The overlap region may include an aperture-defining spacer layer, and/or an impedance element, such as a porous membrane, adapted to distribute at least one fluid across the entire width of the outlet channel to promote reliable fluid mixing.

11 Claims, 11 Drawing Sheets

U.S. PATENT DOCUMENTS

| | | | |
|---|---|---|---|
| 5,595,712 A | 1/1997 | Harbster et al. | 422/129 |
| 5,640,995 A | 6/1997 | Packard et al. | 137/597 |
| 5,646,039 A | 7/1997 | Northrup et al. | 435/287.2 |
| 5,658,515 A | 8/1997 | Lee et al. | 264/219 |
| 5,690,763 A | 11/1997 | Ashmead et al. | 156/60 |
| 5,698,299 A | 12/1997 | Schmidt et al. | 428/209 |
| 5,771,810 A | 6/1998 | Wolcott | 101/483 |
| 5,842,787 A | 12/1998 | Kopf-Sill et al. | 366/340 |
| 5,849,208 A | 12/1998 | Hayes et al. | 216/94 |
| 5,858,188 A | 1/1999 | Soane et al. | 204/454 |
| 5,869,004 A | 2/1999 | Parce et al. | 422/100 |
| 5,872,010 A | 2/1999 | Karger et al. | 436/173 |
| 5,882,465 A | 3/1999 | McReynolds | 156/285 |
| 5,882,571 A | 3/1999 | Kaltenbach et al. | 264/400 |
| 5,904,424 A | 5/1999 | Schwesinger et al. | 366/336 |
| 5,904,824 A | 5/1999 | Oh | 204/601 |
| 5,921,678 A | 7/1999 | Desai et al. | 366/336 |
| 5,922,591 A | 7/1999 | Anderson et al. | 435/287.2 |
| 5,932,315 A | 8/1999 | Lum et al. | 428/172 |
| 5,932,799 A | 8/1999 | Moles | 73/53.01 |
| 5,945,203 A | 8/1999 | Soane | 428/209 |
| 6,004,515 A | 12/1999 | Parce et al. | 422/100 |
| 6,007,775 A | 12/1999 | Yager | 422/57 |
| 6,030,581 A | 2/2000 | Virtanen | 422/68.1 |
| 6,074,725 A | 6/2000 | Kennedy | 428/188 |
| 6,136,272 A | 10/2000 | Weigl et al. | 422/82.05 |
| 6,186,660 B1 | 2/2001 | Kopf-Sill et al. | 366/340 |
| 6,190,034 B1 | 2/2001 | Nielsen et al. | 366/336 |
| 6,193,471 B1 | 2/2001 | Paul | 417/53 |
| 6,235,471 B1 | 5/2001 | Knapp et al. | 435/6 |
| 6,264,900 B1 | 7/2001 | Schubert et al. | 422/224 |
| 6,287,520 B1 | 9/2001 | Parce et al. | 422/100 |
| 6,296,020 B1 | 10/2001 | McNeely et al. | 137/806 |
| 6,409,832 B2 | 6/2002 | Weigl et al. | 117/206 |
| 6,418,968 B1 * | 7/2002 | Pezzuto et al. | 137/833 |
| 6,482,306 B1 | 11/2002 | Yager et al. | 204/600 |
| 6,494,614 B1 | 12/2002 | Bennett et al. | 366/336 |
| 6,537,506 B1 | 3/2003 | Schwalbe et al. | 422/130 |
| 2001/0048637 A1 | 12/2001 | Weigl et al. | 366/341 |
| 2001/0048900 A1 | 12/2001 | Bardell et al. | 422/100 |
| 2002/0048535 A1 | 4/2002 | Weigl et al. | 422/100 |
| 2002/0076350 A1 | 6/2002 | Weigl et al. | 422/58 |
| 2002/0187074 A1 * | 12/2002 | O'Connor et al. | 422/82.05 |
| 2002/0192701 A1 | 12/2002 | Adey | 435/6 |
| 2003/0123322 A1 | 7/2003 | Chung et al. | 366/165.1 |

OTHER PUBLICATIONS

Jacoby, Mitch, *Chemistry Flows Like Clockwork—Flow system used to make simple devices for time–dependent studies,*"Chemical & Engineering News," Feb. 24, 2003, p. 5.

Deshmukh, Ajay A., et al., A.P. (2000), "Continuous Micromixer with Pulsatile Micropumps," Solid–State Sensor and Actuator Workshop, Hilton Head Island, SC, USA, Jun. 4–8, 2000, pp. 73–76.

Martin, P.M., et al., *Laser micromachined and laminated microchannel components for chemical sensors and heat transfer applications,* "Micromachined Devices and Components III," SPIE—The International Society for Optical Engineering, vol. 3224, Bellingham, Washington, USA, pp. 258–265.

Tracey, M.C., et al., "Microfluidic Mixer Employing Temporally–Interleaved Liquid Slugs and Parabolic Flow," *Micro Total Analysis Systems,* J.M. Ramsey and A. van den Berg (eds.), 2001 Kluwer Academic Publishers, Netherlands, pp. 141–142.

Ehrfeld, Wolfgang, et al., "Injection of Many Small Substreams of One Component into a Main Stream of Another Component," *Microreactors—New Technology for Modern Chemistry,* Vch Verlagsgesellschaft Mbh; $1^{st}$ edition, Jun. 15, 2000, pp. 53–55.

Liu, Robin H., et al., "Plastic In–Line Chaotic Micromixer for Biological Application," *Micro Total Analysis Systems,* J.M. Ramsey and A. van den Berg (eds.), 2001 Kluwer Academic Publishers, Netherlands, pp. 163–164.

Ehrfeld, W., et al., *Potentials and Realization of Microreactors,*"DECHEMA Monographs," vol. 132, VCH Verlagsgesellschaft, 1996, pp. 1–28.

Johnson, Timothy J., et al., *Rapid Microfluidic Mixing,* "Analytical Chemistry," vol. 74, No. 1., Jan. 1, 2002, pp. 45–51.

Verpoorte, Elisabeth M. J., et al., "Silicon–Based Chemical Microsensors and Microsystems," *Interfacial Design and Chemical Sensing,* American Chemical Society 1994, Chapter 21, pp. 244–254.

Bertsch, Arnaud, et al., *Static micromixers based on large–scale industrial mixer geometry,* "Lab on a Chip," The Royal Society of Chemistry, 2001, 1, pp. 56–60.

Branebjerg, Jens, et al., "Fast Mixing by Lamination," Proc. Micro Electro Mechanical Systems Workshop, pp. 441–446, IEEE (1996).

Miyake, Ryo, et al., "Micro Mixer with Fast Diffusion," Proc. Micro Electro Mechanical Systems Workshop, pp. 248–253, IEEE (1993).

Mensinger, H., et al., "Microreactor With Integrated Static Mixer and Analysis System," Micro Total Analysis Systems, pp. 237–240, Kluwer, The Netherlands (1995).

Larsen, Ulrik D., et al.. "Fast Mixing by Parallel Multilayer Lamination," Analytical Methods & Instrumentation, Proc. $2^{nd}$ International Symposium Miniaturized Total Analysis Systems μTAS–96, pp. 228–230 (1996).

Merkel, Tobias, et al., "A New Technology for Fluidic Microsystems Based on PCB Technology," Sensors and Actuators 77 A:Physical, pp. 98–105, 1999.

Knight, James B., et al., "Hydrodynamic Focusing on a Silicon Chip: Mixing Nanoliters in Microseconds," Physical Review Letters, vol. 80, No. 17, Apr. 27, 1998.

Bökenkamp, Dirk, et al., "Microfabricated Silicon Mixers for Submillisecond Quench–Flow Analysis," Anal. Chem. 70, pp. 232–236, 1998.

Svasek,P., et al., "Dry Film Resist Based Fluid Handling Components for μTAS" Institute für Allgemeine Elektrotechnik und Elektronik, Technische Universität Wien, undated.

Shoji, Shuichi, "Fluids for Sensor Systems," Topics in Current Chemistry, vol. 194, 1998.

McNeely, Michael R., et al., "Hydrophobic Microfluidics," SPIE Microfluidic Devices & Systems II, vol. 3877, Sep. 1999.

Desai, Amish et al., "Microfluidic Sub–millisecond Mixers For The Study of Chemical Reaction Kinetics," Transducers 97 (1997 Int'l Conf. on Solid–State Sensors and Actuators), vol. 1, pp. 167–170, Jun. 16–19, 1997.

Weigl, Bernhard H., et al., "Passive Microfluidics–Ultra–low–cost plastic disposable lab–on–a–chip," μ–TAS 2000, Twente, the Netherlands, May 14–18, 2000.

Ehrfeld, Wolfgang et al., "Characterization of Mixing in Micromixers by a Test Reaction: Single Mixing Units and Mixer Arrays," Ind. Eng. Chem. Res. 1999, 38, 1075–1082, Jan. 23, 1999.

Voldman, Joel, et al., "An Integrated Liquid Mixer/Valve," Journal of Microelectromechanical Sys., vol. 9, No. 3, Sep. 2000.

Yang, Xing, et al., "A MEMS Thermopneumatic Silicone Membrane Valve" (1998) Sensors and Actuators A: Physical, vol. 64, pp. 101–108.

Schulte, Thomas, "The Development of Practical Microfluidic–Based Systems for Chemical and Blood Analysis" (1999) in Drug Discovery Technology for the New Millennium Chapter 13, pp. 127–135. Conference proceeding: IBC USA Conferences, Inc.:$4^{th}$ Annual Conference on Microfabrication and Microfluidic Technologies.

Becker, Holger, et al., "Silicon as Tool Material for Polymer Hot Embossing", (1999) Proceedings MEMS '99 Orlando, 228–231.

Jeon, Noo Li, et al., "Large–Area Patterning by Vacuum–Assisted Micromolding" (1999) Adv. Mater. 11, No. 11:946–950.

Jackman, Rebecca J., et al., "Electrochemistry and soft lithograph: A route to 3–D microstructures", (May 1999) Chemtech 18–30.

Folch, A., et al., "Molding of Deep Polydimethylsiloxane Microstructures for Microfluidics and Biological Applications" (Feb. 1999) Journal of Biomechanical Engineering 121:28–34.

Duffy, David C., et al., "Rapid Prototyping of Microfluidic Systems, in Poly(dimethylsiloxane)", (Dec. 1998) Analytical Chemistry 70:4974–4984.

Grzybowski, B. A., et al., "Generation of Micrometer–Sized Patterns for Micranalytical Applications Using a Laser Direct–Write Method and Microcontact Printing", (Nov. 1998) Analytical Chemistry 70:4645–4652.

Gonzalez, C., et al., "Fluidic interconnects for modular assembly of Chemical Microsystems", (Jan. 1998) Sensors and Actuators B 49:40–45.

Qin, Dong, et al., "Microfabrication, Microstructures and Microsystems", (1998) Topics in Current Chemistry 194:1–19.

Fuhr, G., et al., "Biological Application of Microstructures", (1998) Topics in Current Chemistry 194:83–116.

Shoji, Shuichi, "Fluids for Sensor Systems", (1998) Topics in Current Chemistry 194:163–188.

Cordova, Emilio, et al., "Noncovalent Polycationic Coatings for Capillaries in Capillary Electrophoresis of Proteins" (Apr. 1997) Analytical Chemistry 69:1370–1379.

McCormick, Randy M., et al., "Microchannel Electrophoretic Separations of DNA in Injection–Molded Plastic Substrates" (Dec. 1997) Analytical Chemistry 69:2626–2630.

Martynova, Larisa et al., "Fabrication of Plastic Microfluid Channels by Imprinting Methods" (1997) Anal. Chem. 69:4783–4789.

Kovacs, Gregory T.A., et al., "Silicon Micromachining Sensors to Systems" (Jul. 1996) Analytical Chemistry News & Features 407A–412A.

Shoji, Suchi, et al., "Microflow Devices and Systems" (Oct. 1994) J. Micromech. Microeng. 4:157–171.

Schomburg, W.K., et al., "Microfluidic Components in LIGA Technique" (Feb. 1994) J. Micromech.Microeng. 4:186–191.

Verpoorte, Elisabeth M.J., et al., "Three–Dimensional Micro Flow Manifolds for Miniaturized Chemical Analysis Systems" (Oct. 1994) J. Micromech. Microeng. 4:246–256.

* cited by examiner

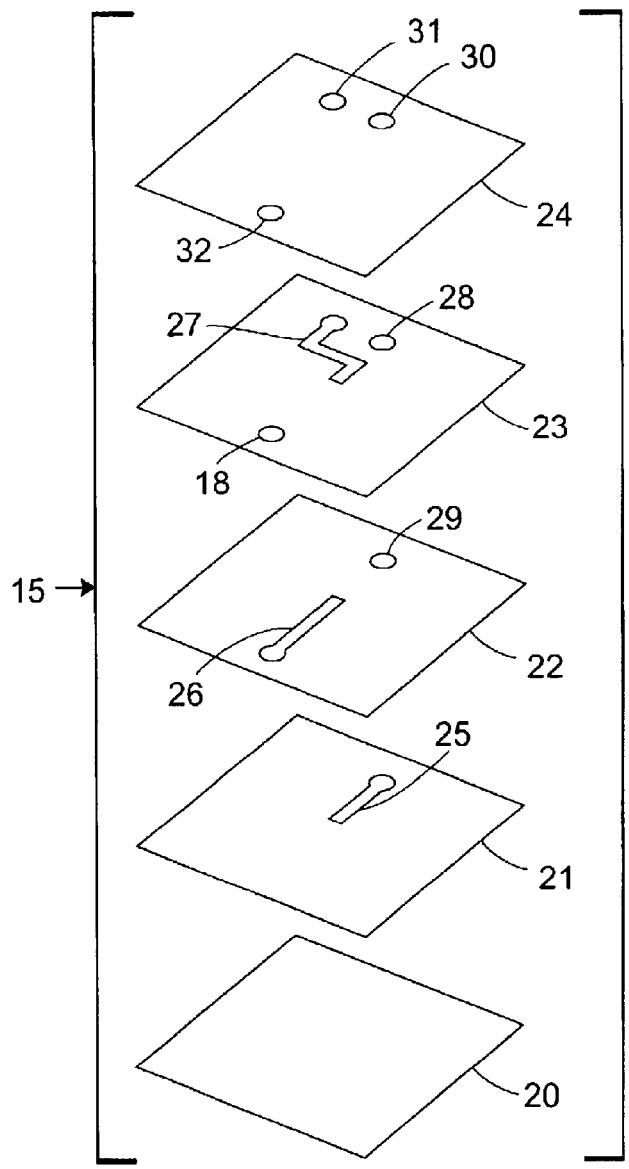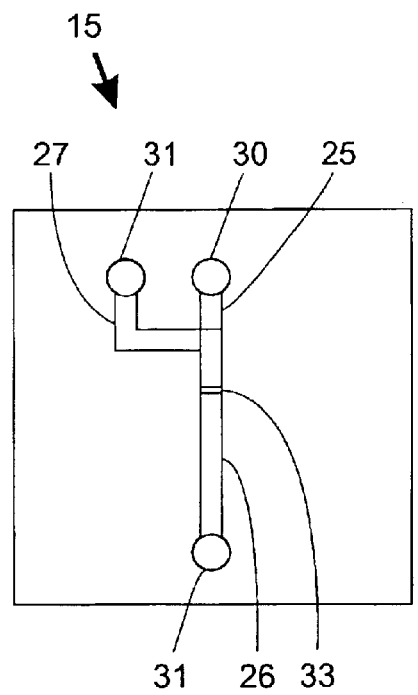
FIG._1A
FIG._1B

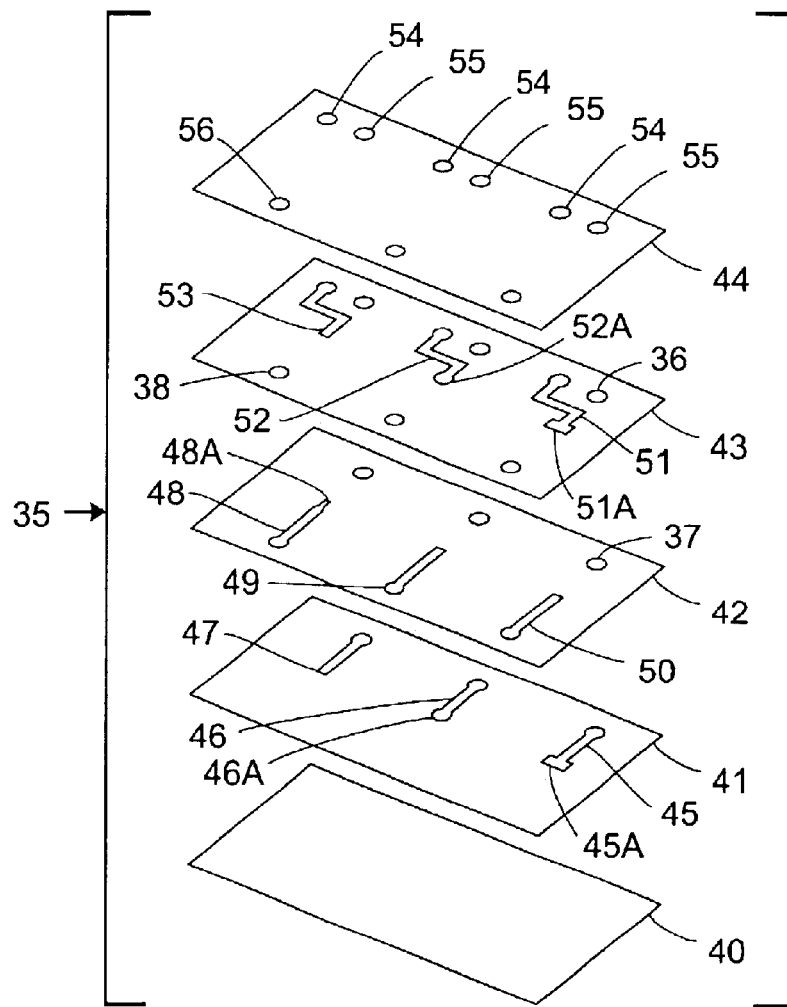
FIG._2A
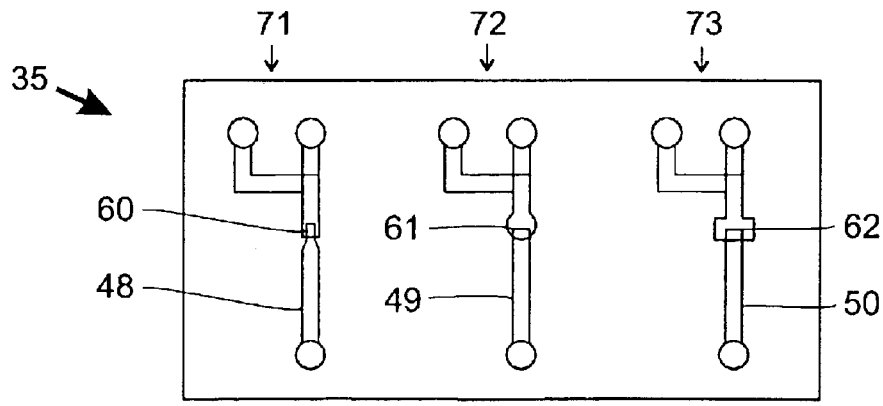
FIG._2B

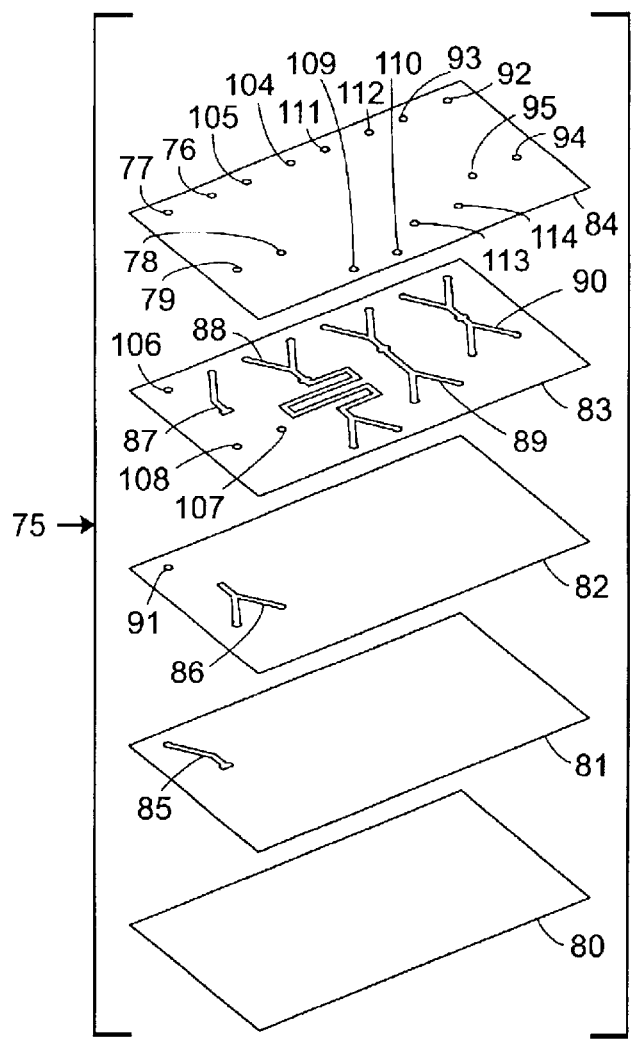
FIG._3A
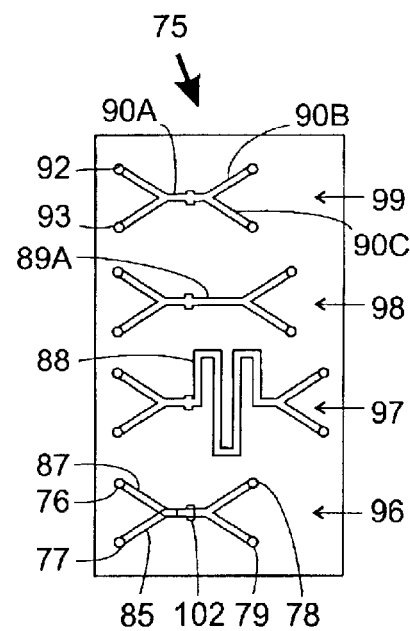
FIG._3B

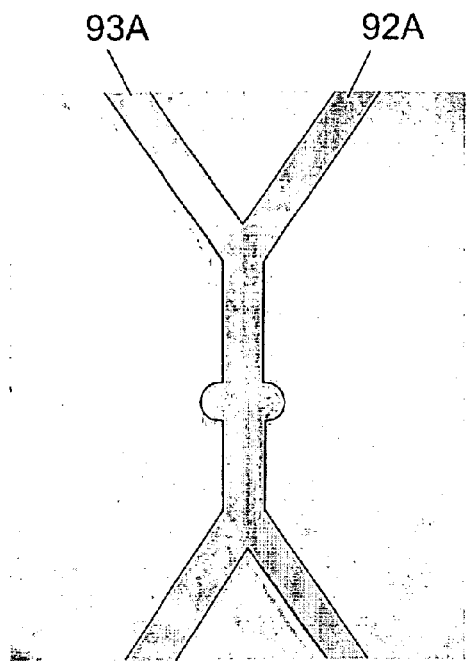
FIG._ 4A
99
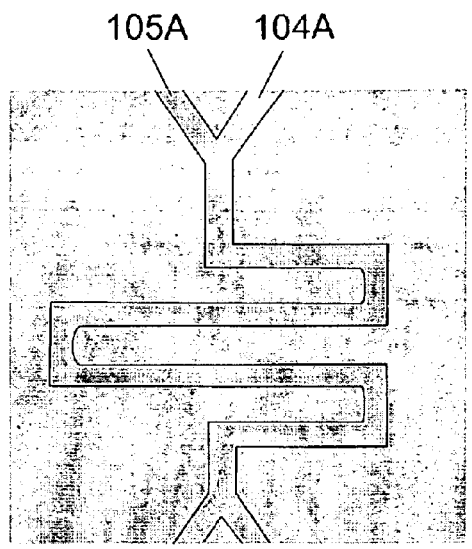
FIG._ 4B
97
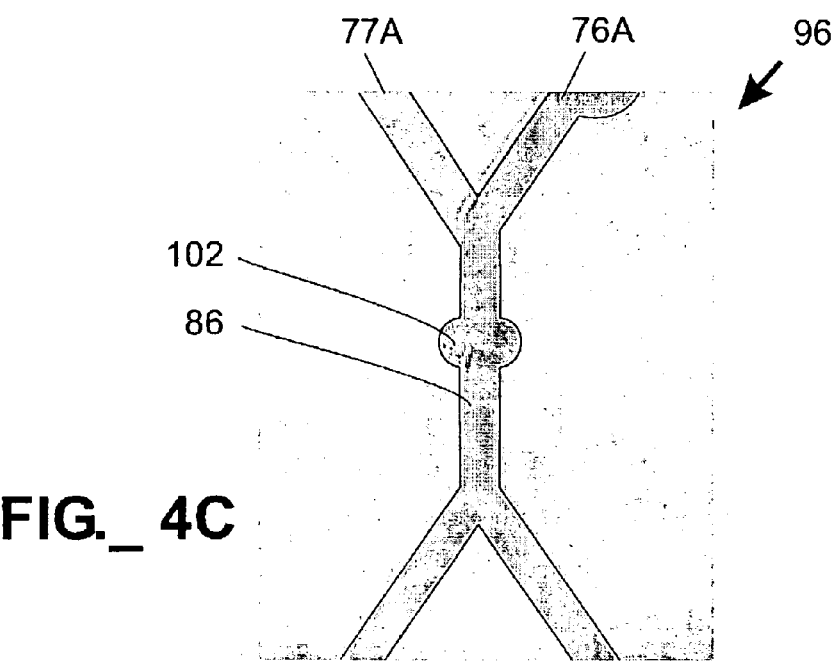
FIG._ 4C

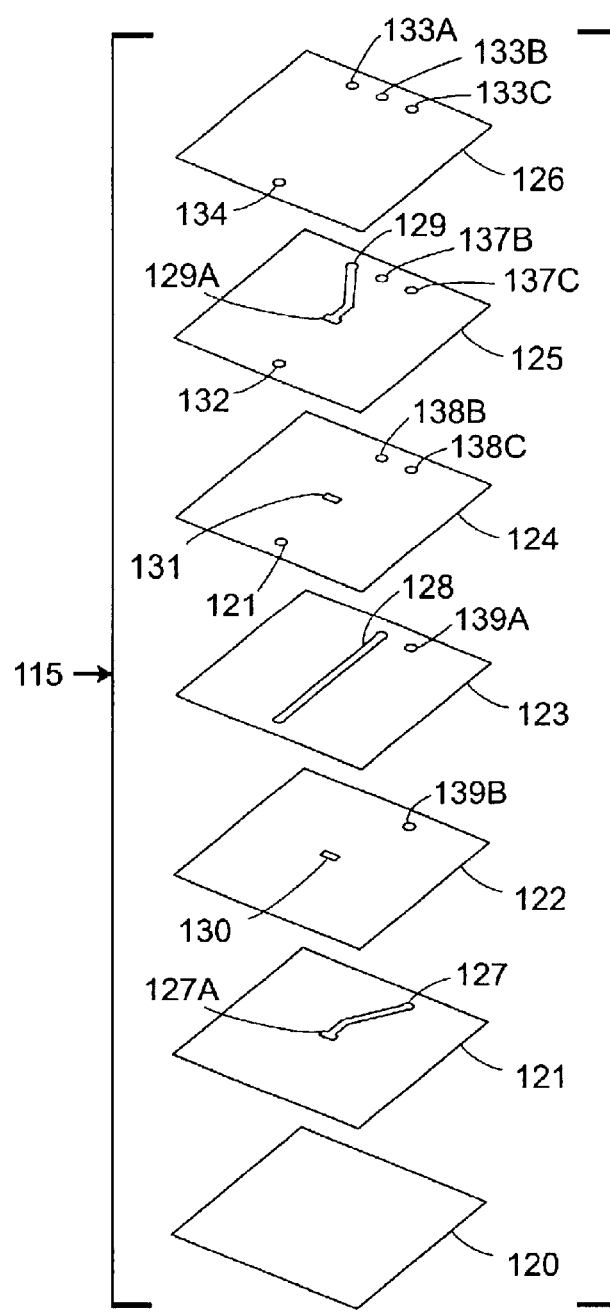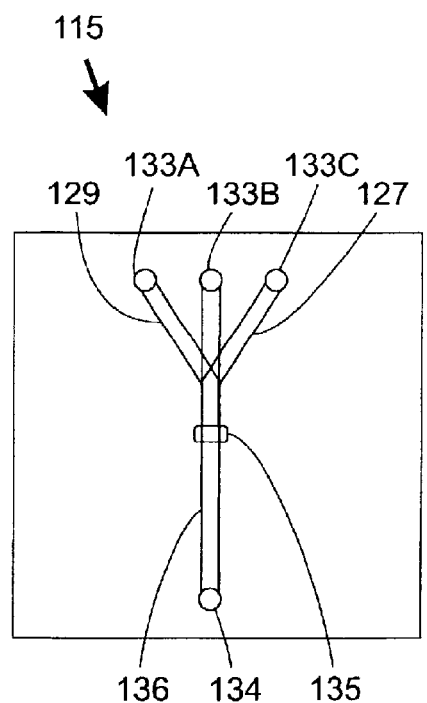
FIG._5A
FIG._5B

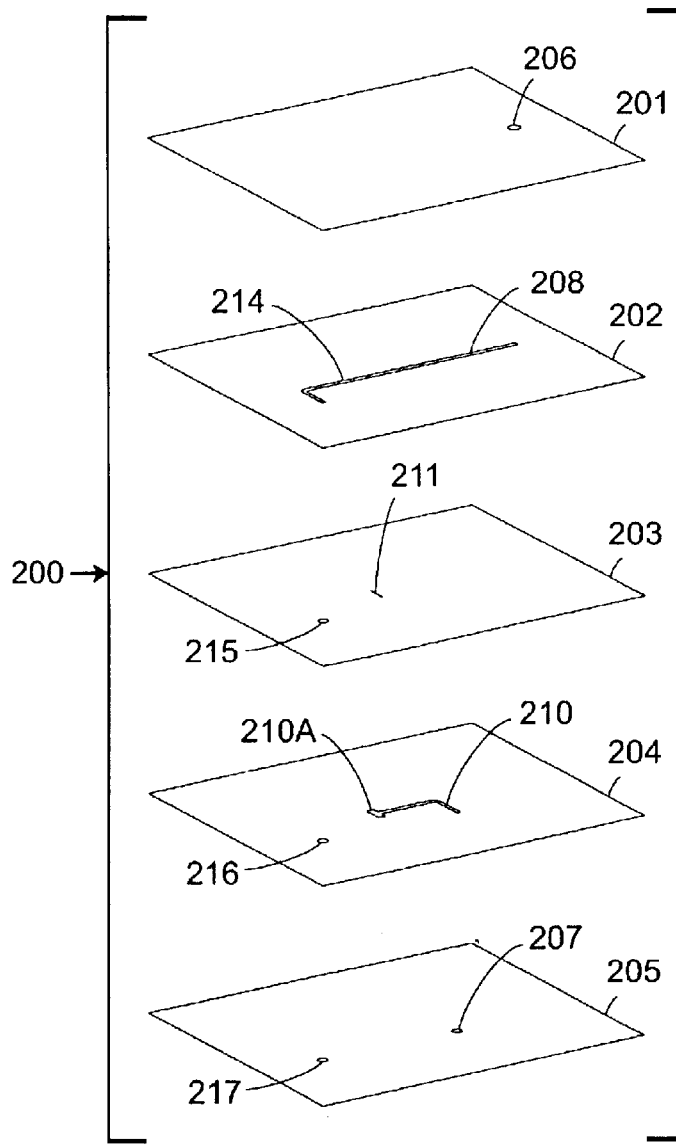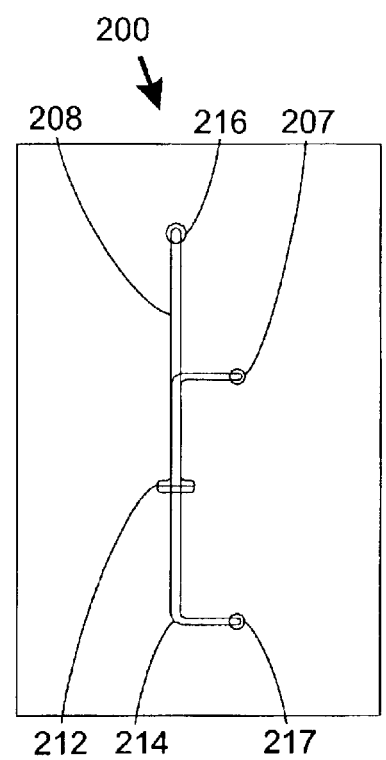
FIG._6A
FIG._6B

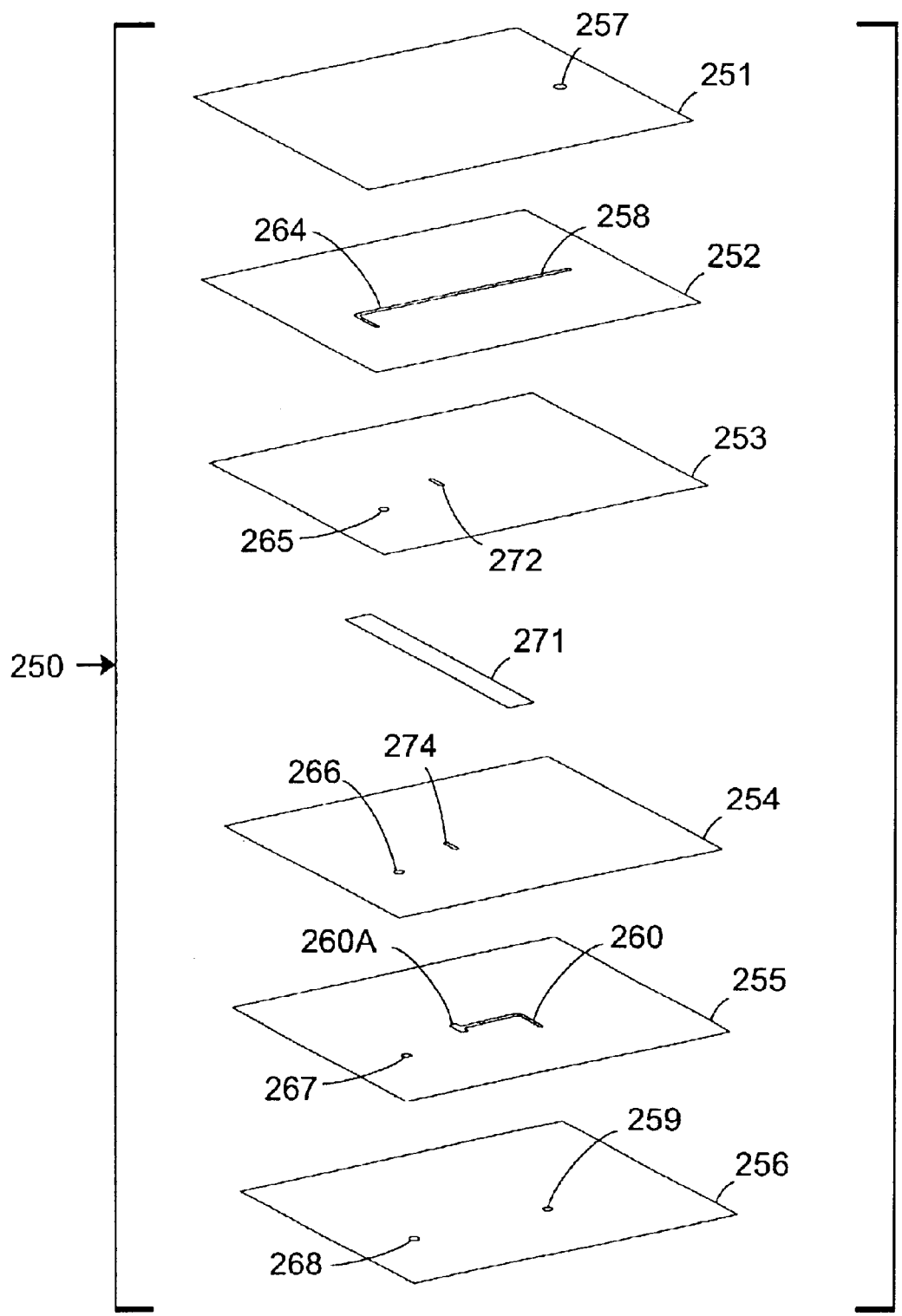
FIG._8A

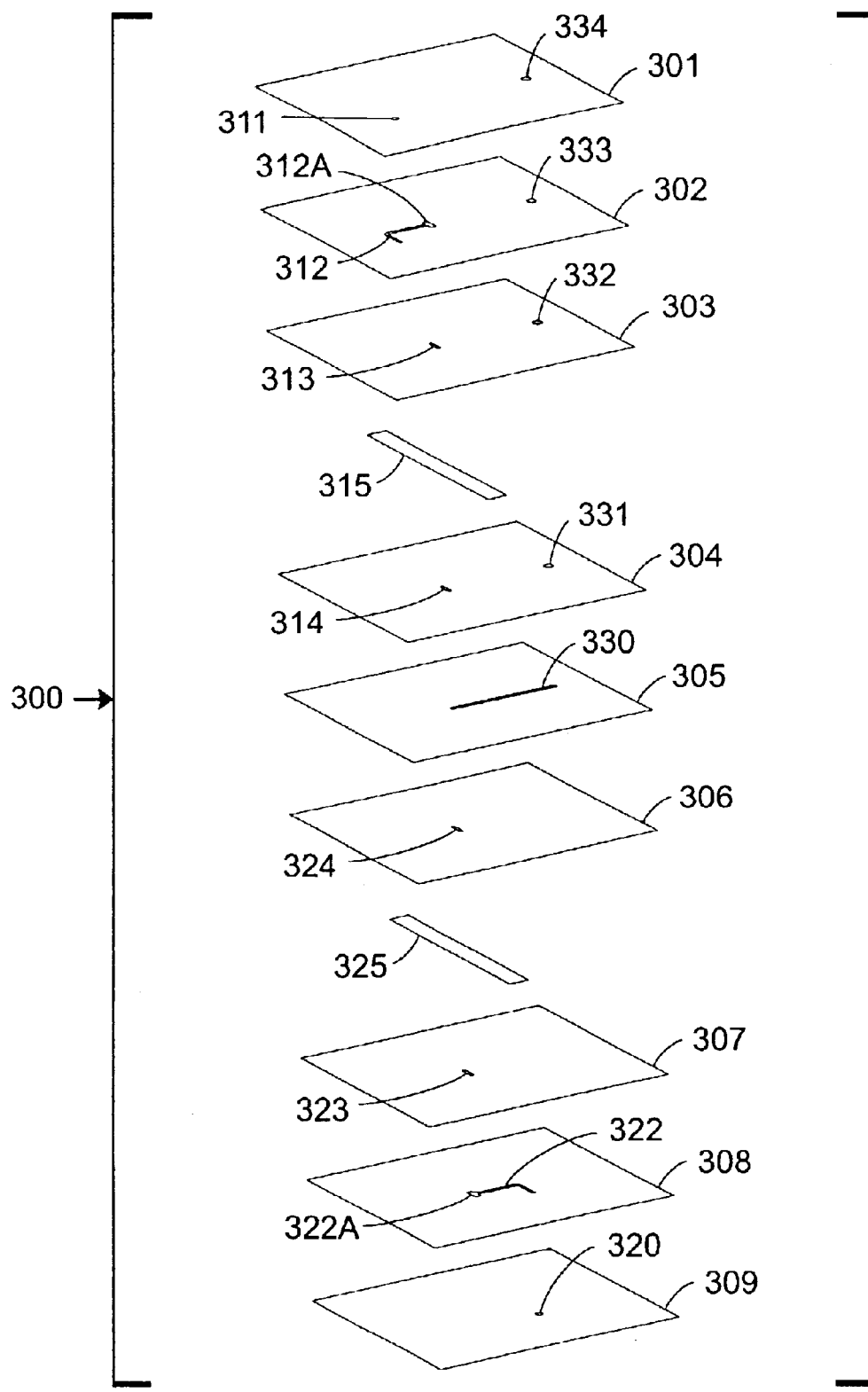
FIG._9

FLUIDIC MIXER IN MICROFLUIDIC SYSTEM

STATEMENT OF RELATED APPLICATION(S)

The present application is a continuation-in-part of U.S. patent application Ser. No. 09/632,681, filed Aug. 7, 2000 now abandoned.

FIELD OF THE INVENTION

The present invention relates to microfluidic devices and the mixing of fluids within those devices. Such devices are useful in, for example, various biological and chemical systems, as well as in combination with other liquid-distribution devices.

BACKGROUND OF THE INVENTION

There has been a growing interest in the manufacture and use of microfluidic systems for the acquisition of chemical and biological information. In particular, microfluidic systems allow complicated biochemical reactions to be carried out using very small volumes of liquid. These miniaturized systems improve the response time of reactions, minimize sample volume, and lower reagent cost.

Traditionally, microfluidic systems have been constructed in a planar fashion using silicon fabrication techniques. Representative systems are described, for example, by Manz et al. (Trends in Anal. Chem. (1990) 10(5): 144–149; Advances in Chromatography (1993) 33: 1–66). Typically, such microfluidic devices are constructed using photolithography to define channels on silicon or glass substrates, followed by the use of etching techniques to remove material from the substrate to form the channels. A cover plate is bonded to the top of this device to provide closure. Metals may also be used to fabricate microfluidic devices. More recently, other methods have been developed that allow microfluidic devices to be constructed from plastic, silicone or other polymeric materials. In most instances, however, these techniques do not lend themselves to rapid prototyping and manufacturing flexibility. Moreover, the tool-up costs for such techniques are often quite high and can be cost-prohibitive.

Generally, the mixing of fluids in a microfluidic system is problematic, since fluid flow within these devices is not turbulent. Some microfluidic mixing devices have been constructed in substantially planar microfluidic systems having channels defined in the surface (e.g., by micromachining) of a common substrate, where the fluids are allowed to mix through diffusion (see Bokenkamp et al., Analytical Chemistry (1998) 70(2): 232–236). In these systems, the fluids mix only along a lateral interface, which is commonly small relative to the overall volume of the fluids. Thus, very little mixing occurs within a reasonable period of time.

Alternative mixing methods have been developed based on electrokinetic flow. Systems providing such utility are complicated and require electrical contacts and associated controls. Additionally such systems only work with charged fluids, or fluids containing electrolytes. Finally, these systems require voltages that are sufficiently high as to cause electrolysis of water, thus forming bubbles that complicate the collection of samples without destroying them.

Thus, there is a need for mixing devices capable of thoroughly and rapidly mixing a wide variety of fluids in a microfluidic environment. It would also be desirable for such devices to be inexpensive and simple to fabricate, yet be robust enough to mix fluids reliably both over a wide variety of flow conditions and in spite of slight variations in device assembly due to manufacturing tolerances.

BRIEF DESCRIPTION OF THE DRAWINGS

FIG. 1A is an exploded perspective view of a microfluidic device capable of mixing two fluids, the device constructed with five substantially planar sheets of material, including three stencil sheets, and having a channel overlap region. FIG. 1B is a top view of the assembled device of FIG. 1A.

FIG. 2A is an exploded perspective view of a microfluidic device constructed with five substantially planar sheets of material, including three stencil sheets, the device having three distinct fluid mixer portions each demonstrating a different channel overlap geometry. FIG. 2B is a top view of the assembled device of FIG. 2A.

FIG. 3A is an exploded perspective view of a microfluidic device constructed with five substantially planar sheets of material, including three stencil sheets, the device having one overlap-type fluid mixer portion and three different non-overlap-type portions for contacting different fluid streams but relatively ineffective for mixing them. FIG. 3B is a top view of the assembled device of FIG. 3A.

FIG. 4A is a top view micrograph with traced channel borderlines of a first portion of the device illustrated in FIGS. 3A–3B in operation, in which two fluids flow side-by-side in interfacial contact in a straight central channel but only minimal mixing results between the two fluids before the aggregate is split into separate streams. FIG. 4B is a top view micrograph with traced channel borderlines of a second portion of the device illustrated in FIGS. 3A–3B in operation, in which two fluids flow side-by-side in interfacial contact in a channel with several turns but only minimal mixing results between the two fluids before the aggregate is split into two separate streams. FIG. 4C is a top view micrograph of a with traced channel borderlines of a third portion of the device illustrated in FIGS. 3A–3B in operation, in which one fluid is layered atop the other fluid at an overlap region and rapid mixing results between the two fluids before the aggregate is split into separate streams.

FIG. 5A is an exploded perspective view of a microfluidic device constructed with seven substantially planar sheets of material, including multiple stencil sheets, the device being capable of overlapping three fluids in stacked horizontal layers to promote fluid mixing. FIG. 5B is a top view of the assembled device of FIG. 5A.

FIG. 6A is an exploded perspective view of a microfluidic mixing device constructed with five substantially planar sheets of material, including multiple stencil sheets, the device having an overlap region including a slit. FIG. 6B is a top view of the assembled device of FIG. 6A.

FIG. 8A is an exploded perspective view of a microfluidic mixing device constructed with six substantially planar sheets of material, including multiple stencil sheets, the device having a porous membrane disposed at an overlap region.

FIG. 9 is an exploded perspective view of a microfluidic mixing device constructed with nine substantially planar sheets of material, including multiple stencil sheets, the device having a two porous membrane disposed at an overlap region.

DETAILED DESCRIPTION OF PREFERRED EMBODIMENTS OF THE INVENTION

Definitions

Figure 7A:
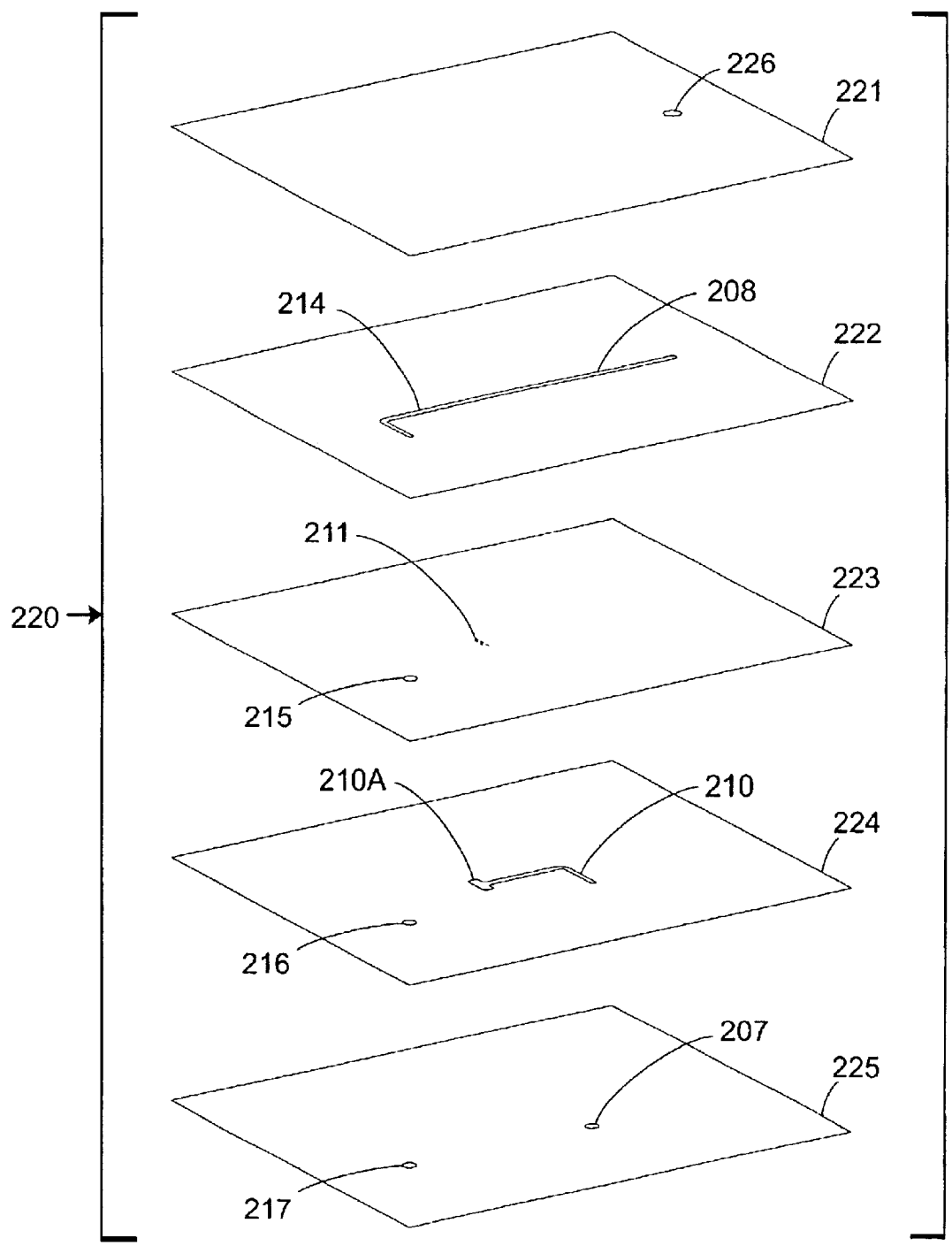
FIG. 7A is an exploded perspective view of a microfluidic mixing device constructed with five substantially planar sheets of material, including multiple stencil sheets, the device having an overlap region including several staggered apertures arranged in an uninterrupted fashion to span across the entire width of the outlet channel.

The term "channel" as used herein is to be interpreted in a broad sense. Thus, it is not intended to be restricted to elongated configurations where the transverse or longitudinal dimension greatly exceeds the diameter or cross-sectional dimension. Rather, this term is meant to comprise cavities or tunnels of any desired shape or configuration through which liquids may be directed. Such a fluid cavity may, for example, comprise a flow-through cell where fluid is to be continually passed or, alternatively, a chamber for holding a specified, discrete amount of fluid for a specified amount of time. "Channels" may be filled or may contain internal structures comprising valves or equivalent components.

The term "microfluidic" as used herein refers to structures or devices through which one or more fluids are capable of being passed or directed and having at least one dimension less than about 500 microns.

The term "sheet" as used herein refers to a discrete, preferably substantially planar layer of material having an upper surface, an opposing lower surface, at least one edge, and a thickness.

The terms "stencil" or "stencil sheet" as used herein refer to a sheet of material that is preferably substantially planar through which one or more variously shaped and oriented portions have been cut or otherwise removed through the entire thickness of the sheet, and that permits substantial fluid movement within the sheet (e.g., in the form of channels or chambers, as opposed to simple through-holes for transmitting fluid through one sheet to another sheet). The outlines of the cut or otherwise removed portions form the lateral boundaries of microstructures that are formed when a stencil sheet is sandwiched between other sheets such as substrates (whether or not containing through-holes) and/or other stencil sheets.

Microfluidic Device Fabrication

As indicated previously, various microfluidic device fabrication techniques are known. In preferred embodiments, fluidic devices are constructed using stencil sheets to define channels and/or other microstructures. For example, a computer-controlled plotter modified to accept a cutting blade may be used to cut various patterns through a sheet of material. Such a blade may be used either to cut sections to be detached and removed from the stencil sheets, or to fashion slits that separate certain regions of a sheet without removing any material. Alternatively, a computer-controlled laser cutter may be used to cut portions through a sheet of material. While laser cutting may be used to yield precisely-dimensioned microstructures, the use of a laser to cut portions of a stencil sheet inherently involves the removal of some material. Further examples of methods that may be employed to form stencil sheets include conventional stamping or die-cutting technologies. Various additional methods of stencil fabrication are set forth in commonly assigned published WIPO international application no. WO 01/25138, published Oct. 4, 2000. The above-mentioned methods for cutting through a stencil sheet permits robust devices to be fabricated quickly and inexpensively compared to conventional surface micromachining or material deposition techniques that are conventionally employed to produce microfluidic devices.

Microfluidic channels have at least one dimension less than about 500 microns. To provide effective mixing, channels should also have an aspect ratio that maximizes surface-to-surface contact between fluid streams. A channel a provided herein may have a substantially rectangular or square cross-section, with a depth from about 1 to about 500 microns, preferably from about 10 to about 100 microns, and a width of about 10 to about 10,000 microns such that at the overlap region where the channels meet, the aspect ratio (width/depth) of the channel cross section is preferably at least about 2, more preferably at least about 10.

After a portion of a stencil sheet is cut or removed, the outlines of the cut or otherwise removed portions form the lateral boundaries of microstructures that are completed upon sandwiching a stencil sheet between substrates and/or other stencil sheets. The thickness or height of the microstructures such as channels or chambers can be varied by altering the thickness of the stencil sheet, or by using multiple substantially identical stencil sheets stacked on top of one another. When assembled in a microfluidic device, the top and bottom surfaces of stencil sheets are intended to mate with one or more adjacent sheets (such as stencil sheets, spacer sheets, or substrates) to form a substantially enclosed device, typically having at least one inlet port and at least one outlet port.

Various means may be used to seal or bond sheets together. For example, adhesives may be used. In one embodiment, one or more sheets may be fabricated from single-or double-sided adhesive tape, although other methods of adhering sheets together may be used. A portion of the tape (of the desired shape and dimensions) can be cut and removed to form channels, chambers, and/or apertures. A tape-based stencil sheet can then be placed on a supporting substrate with an appropriate cover sheet, between sheets of tape, or between sheets of other materials. In one embodiment, stencil sheets can be stacked on each other. In this embodiment, the thickness or height of the channels within a particular stencil sheet can be varied by varying the thickness of the stencil sheet (e.g., the tape carrier and the adhesive material thereon) or by using multiple substantially identical stencil sheets stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thicknesses of these carrier materials and adhesives may be varied. Alternatively, stencil sheets may be held together using gaskets and/or mechanical force.

In another embodiment, sheets of material may be directly bonded without using adhesives to provide high bond strength (which is especially desirable for high-pressure applications) and eliminate potential compatibility problems between such adhesives and solvents and/or samples. Specific examples of methods for directly bonding sheets of unoriented polypropylene to form stencil-based microfluidic structures are disclosed in commonly assigned U.S. Pat. No. 6,848,462, which is incorporated by reference as if fully set forth herein. In one embodiment, multiple sheets of 7.5-mil (188 micron) thickness "Clear Tear Seal" polypropylene (American Profol, Cedar Rapids, Iowa) including at least one stencil sheet may be stacked together, placed between glass platens and compressed to apply a pressure of 0.26 psi (1.79 kPa) to the layered stack, and then heated in an industrial oven for a period of approximately 5 hours at a temperature of 154° C. to yield a permanently bonded microstructure well-suited for use with high-pressure column packing methods. In another embodiment, multiple sheets of 7.5-mil (188 micron) thickness "Clear Tear Seal" polypropylene (American Profol, Cedar Rapids, Iowa) including at least one stencil sheet may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

Stencil-based fabrication methods also permit devices to be fabricated with a wide variety of different materials, which permit devices to accommodate a vast array of liquid reagents or solutions. Different types of solvents and samples can be mixed, including but not limited to water-based systems, organic-based systems, biological materials solvated or dispersed within solvent, and various chemical systems. Preferable materials for constructing microfluidic devices according to the present invention include paper, foil or plastics. Examples of plastics include those selected from the group consisting of polytetrafluoroethylenes, polycarbonates, polypropylenes, polyimide and polyesters.

Microfluidic Mixers Generally

Microfluidic mixing devices according to the present invention include at least two inlet channels defined in different stencil sheets of a microfluidic device. The sheets may be horizontally disposed, such that a first channel lies substantially within a horizontal plane, and a second channel defined in an adjacent sheet can be disposed above or below the first channel. The sheets containing the inlet channels can be adjacent or can be separated by one or more spacer sheets. The inlet channels meet or intersect at an overlap region that is also in fluid communication with an outlet channel, such that introduced from the inlet channels proceed into the outlet channel. The outlet channel can be defined in the same stencil sheet as one inlet channel, or the outlet channel can be defined in a different sheet. Where the inlet channels are separated by more than one intervening spacer sheet, apertures in the intervening spacer sheets can extend an inlet channel to form the overlap region.

Preferably, microfluidic mixing devices according to the present invention that provide rapid mixing of two or more fluids, and are capable of mixing various fluids in a controlled manner based on the design and construction of the devices. Inlet channels defined in different sheets of material intersect in certain areas in order to promote mixing of the fluids an outlet channel. Factors including the amount of overlap, geometry of the overlaps, surface chemistry of the overlaps, fluid used and flow rate of the fluids may be varied to controllably affect the mixing characteristics.

In one embodiment, a microfluidic device according to the present invention includes at least two inlet channels defined in different substantially planar, horizontally disposed, sheets of the device. Such sheets can be flexible, to permit the overall device to conform to a non-planar shape and remain operable. The sheets defining the inlet channels can be adjacent or can be separated by one or more (e.g., spacer) sheets. The inlet channels meet at an overlap region. Channels defined in adjacent stencil sheets should not overlap vertically until the overlap region, unless an intermediate layer is used. An outlet channel is in fluid communication with the overlap region, such that fluid flowing through the inlet channels enters the overlap region and exits through the outlet channel.

The materials of the sheets used within a device may or may not be the same. For example, one sheet may be made of a hydrophobic material whereas another sheet may be made of a hydrophilic material. The sheets may be made of materials that expedite fluid flow through the channels. Thus, the materials of individual sheets may be selected depending on the composition and chemical nature of the fluid flowing through individual channels.

Preferably, a microfluidic device includes a first inlet that is substantially parallel to the top and the bottom surfaces of a first sheet, a second inlet channel that is substantially parallel to the top and the bottom surfaces of a second sheet, and an overlap region in which said first and second inlet channels are in fluid communication with each other and with an outlet channel. In different embodiments, the outlet channel is may be formed in the first sheet, the second sheet, or a third sheet. Preferably, the first sheet and the second sheet are joined together such that the plane of the joint is substantially parallel to the top and bottom surfaces of the sheets.

In another embodiment, the outlet channel is formed in a third sheet of material such that the outlet channel is in a plane that is substantially parallel to the top and bottom surfaces of the third sheet. Further, the first, second and third sheets are joined together such that the planes of the joints are substantially parallel to the top and bottom surfaces of the sheets. Alternatively, the third sheet may be joined to both the first sheet and the second sheet. An overlap region is formed by the junction between the first and second inlet channels such that a first fluid and second fluid enter the overlap region and mix therein.

The first and second fluids supplied to a mixer may be substantially the same or may differ in one or more of their properties, such as, viscosities, temperatures, flow rates, compositions.

In another embodiment, a device comprises two or more microfluidic inlet channels that are located within different sheets of material composing a three-dimensional device. The inlet channels are designed such that the flows of the fluids overlap, with a membrane or spacer layer separating the fluids from each other, and the flows run substantially in the same direction. The inlet channels end at an overlap region. The combined fluid flow then continues into the outlet channel that begins at the same overlap region. This outlet channel may be disposed in a sheet between the two inlet channels, and is preferably designed such that the direction of the resulting combined fluid flows in the same direction as the inlet fluids. Alternatively, the outlet channel can simply be an extension of one of the inlet channels.

In certain embodiments, a microfluidic device may contains more than one of these fluidic overlaps. In certain embodiments, all of the fluidic mixers are identical. In other embodiments, mixers may differ within a single device in order to produce preferential mixing. In certain embodiments, the mixers may be multiplexed within a device to perform various applications, such as the possibility for combinatorial synthesis of various types of materials.

In one embodiment, a mixing device includes a first channel defined through the entire thickness of a first substantially flat sheet of material such that the first channel is substantially parallel to the top and the bottom surfaces of the first sheet, a second channel defined through the entire thickness of a second substantially flat sheet of material such that the second channel is substantially parallel to the top and the bottom surfaces of the second sheet, a third channel defined through the entire thickness of a third substantially flat sheet of material such that the third channel is substantially parallel to the top and the bottom surfaces of the third sheet, and an overlap region within which the first, second and third inlet channels are in fluid communication with each other. In one version of this embodiment, the first sheet is sandwiched between the second and third sheets whereby the second channel is in fluid communication with the top half of the overlap region and the third channel is in fluid communication with the bottom half of the overlap region.

Traditional, less effective microfluidic mixing devices include fluidic channels defined within a single substantially planar surface of a substrate. Typically, the aspect ratio (width/depth) of these channels is 10:1 or greater, often as high as 500:1 or greater. Such a constraint is in part a limitation of the silicon fabrication techniques used to produce such devices. In order to mix samples, two coplanar inlet channels are brought together into a common outlet channel. The fluids meet at the intersection and proceed through the outlet channel. In microfluidic systems, all fluid flow is laminar (no turbulent flow occurs); thus, any mixing in this outlet channel occurs through diffusional mixing at the interface between the inputted liquid streams. This mixing is extremely slow since the interface between the two intersecting fluids is along the smaller dimensions of the perpendicular cross-sections of the fluid streams and is very small compared to the overall volume of the fluids. Since these traditional microfluidic systems include channels all defined within the same substantially planar surface of the device, this problem is difficult to overcome. Relatively ineffective microfluidic mixers approximating prior art designs but constructed with a stencil fabrication method are provided in three portions of the device 75 illustrated in FIG. 3A-3B.

In devices according to the present invention, fluidic channels are defined in different sheets of a three-dimensional device fabricated with several (i.e., at least four) stacked sheets. When the inlet channels are brought together to converge into a common outlet channel, the interface between the two fluids is along the horizontal dimension of the channels, which is the larger dimension of the perpendicular cross-section of the fluid streams. The larger interface maximizes the diffusion area between the fluids. In this manner, the majority of the volume of the fluids is in very close proximity to the diffusion interface of the mixing fluids and mixing occurs very rapidly. Importantly, the nature of these overlap regions should be carefully controlled in order to optimize the mixing, as will described below.

In certain embodiments, the overlap region comprises one or more spacer sheets containing apertures in fluid communication with the inlet channels. The devices preferably include an upper cover sheet, which may define the top surface of one inlet channel. The devices preferably also include a lower cover sheet, which may define the bottom surface of another inlet channel. In certain embodiments, these upper and lower sheets are substantially rigid.

Example Devices

In the embodiment shown in FIGS. 1A–1B, a microfluidic mixing device 15 is constructed using sandwiched stencil sheets. Referring to FIG. 1A, a microfluidic mixing device 15 is constructed by stacking three stencil sheets 21–23 and sandwiching and adhering them between upper and lower substrates or cover sheets 20, 24. The stencil sheets 21–23 define various channels 25–27 and apertures or through-holes 18, 28, 29. Since the channels 25–27 are defined through the entire thickness of stencil sheets 21–23, respectively, the height of each channel 25–27 is equal to the thickness of its corresponding stencil sheet 21–23. Inlet ports 30, 31 and an outlet port 32 are defined in the upper cover sheet 24. The assembled device 15 is shown in FIG. 1B. In use, a first fluid is injected into a first inlet port 30, passes through through-holes 28, 29 in two sheets 23, 22 and enters an inlet channel 25. A second fluid enters a second inlet port 31 and passes through another inlet channel 27. The two fluids meet at the overlap region or junction 33 shown in FIG. 1B. At this point, the fluids are forced to converge into a single outlet channel 26 defined in a central stencil sheet 22. As the two fluids meet and start to flow into the outlet channel 26, the top half of the outlet channel 26 contains the second fluid and the bottom half contains the first fluid. The heights of these channels 25–27 are relatively small (between 100 nanometers and 500 microns), so diffusional mixing between the tow fluids occurs quickly and a homogenous mixture is transported off-board through the exit port 32. It has been found that the majority of the mixing occurs at the overlap junction 33, with a slight amount of mixing occurring within the outlet channel 26 immediately downstream of the junction 33. The amount of mixing that occurs after the junction 33 depends on a number of factors, including geometry of the channels, chemical make-up of the channels and samples, flow rate, etc.

In the embodiment shown in FIGS. 1A–1B, the three channels 25–27 that meet at the overlap junction 33 are all the same width. Surprisingly, it has been discovered that if the stencil sheets 21–23 containing the channels 25–27 in the device 15 are not well-aligned, then proper mixing does not occur. That is, the entire width of the outlet channel 26 will contain a mixture of the two input fluids downstream of the overlap region 33 only in devices there is a complete overlap between the inlet channels 25, 27 and the outlet channel 26. If, for example, a first inlet channel 25 is misaligned laterally such that for a small portion of the overlap there is an area where only the second inlet channel 27 and the outlet channel 26 overlap, then in this area only the fluid from second inlet channel 27 will enter the outlet channel 26. The remaining area (width) of the outlet channel 26 will contain a mixture of the two input fluids. What results is a "streaking" effect, where a flow of mixed fluids runs parallel with an unmixed fluid through the outlet channel 26. These "streaking" problems are easily overcome by the following modifications.

Additional mixer embodiments are shown in FIGS. 2A–2B. These embodiments do not suffer from the same strict alignment parameters as the mixer 15 shown in FIGS. 1A–1B. Referring to FIG. 2A, three different microfluidic mixers 71–73 are built into a single device 35. The device 35 is constructed from five substantially planar sheets 40–44 including three stencil sheets 41–43. The stencil sheets 41–43 define several channels 45–53 and through holes 36–38 by removal of material through the entire thickness of the appropriate sheet(s). The upper cover sheet 44 defines several inlet ports 54, 55 and exit ports 56, and the lower cover sheet 40 serves to enclose the channels 45–47 defined in the adjacent stencil sheet 41. The stencil sheets 41–43 are adhered together between the cover sheets 40, 44 to form the completed device 35, shown in FIG. 2B. Notice that the shapes of the overlap regions 60–62 in these mixers 71–73 are shaped (e.g., with enlarged end regions 45A, 46A, 51A, 52A and/or reduced end regions 48A) so that slight misalignment of the stencil sheets 41–43 during construction will not necessarily have a detrimental effect on fluid flow and mixing. In other words, each mixer 71–73 of the device 35 is more tolerant of minor fabrication faults (such as may be attributed to manufacturing tolerances) than the previous mixer 15 described in connection with FIGS. 1A–1B. It is believed that the mixers 71–73 such as in FIGS. 2A–2B are far superior to the mixer 15 shown in FIGS. 1A–1B, for the above-outlined reason.

In another embodiment, the overlap junction may be altered by changing the chemical nature in the overlap junction. This can be accomplished by forming a stencil sheet from a different material, or by altering the surface chemistry of a stencil sheet. Surface chemistry can be altered in many ways, as one skilled in the art will realize. Methods of altering the surface chemistry include chemical derivatization as well as surface modification techniques such as plasma cleaning or chemical etching. The chemical derivatization is preferably chosen such that fluids flow through the channels and overlap region occurs smoothly and without bubble formation.

The above-described methods for altering the overlap junction within a microfluidic device can be used independently or in conjunction with one another. Other methods for altering the nature of the junction are also contemplated.

One surprising aspect of overlap-type microfluidic mixers as provided herein is that the optimal parameters for a given overlap may be greatly affected by the nature of the sample that is to be used within the device. It has been found that the optimal geometry for these overlaps changes depending upon the fluids used within the device.

The mixing between fluids supplied from two or more inlet channels can be adjusted to provide a wide range of different ratios of one fluid to the other(s). The main or easiest way to vary the ratio of one fluid to another fluid in a mixture is to hold the flow rate of one fluid (i.e. through one inlet channel) constant, while changing the flow rate of the other fluid (i.e. through another inlet channel). In this way, different mixture ratios may be formed by virtue of different quantities of each liquid entering the mixing chamber or overlap area in a given time period. Another method for changing a mixing ratio is to alter the size of the channels leading into the mixing region; this has the effect of changing the flow rate internally. This may be useful for combinatorial arrays, where different ratios are desired without the hassle of using different external flow rates.

The mixing characteristics of an overlap-type microfluidic mixer were compared to a number of non-overlap-type systems for contacting different fluid streams. Referring to FIGS. 3A–3B, a single device 75 contains four independent microfluidic systems 96–99 was constructed. The device 75 is constructed from five sheets 80–84, including three stencil sheets 81–83 into which channels 85–90 and through holes 91, 106–108 were defined by cutting the various features through the appropriate sheet(s). The stencil sheets 81–83 are constructed with sheets of single sided tape (3 mil polypropylene carrier with water based adhesive on one side) and the channels all have a nominal width of about 45 mils, with certain widened portions having widths of about 60 mils. The bottom cover sheet 80 is 0.25 inch thick acrylic material. Inlet ports 76, 77, 92, 93, 104, 105, 111, 112 and outlet ports 78, 79, 94, 95, 109, 110, 113, 114 are defined in the upper cover sheet 84. All of the ports 76–79, 92–95, 104–105, 109–114 are 60 mils in diameter. The stencil sheets 81–83 are adhered together between the upper and lower cover sheets 80, 84 to form the completed device 75, as shown in FIG. 3B.

In the prior art, microfluidic devices are typically constructed in a two-dimensional fashion, as approximated by the upper three functional portions 97–99 of FIG. 3B. If two different fluids are injected into the two inlet ports 92, 93 of the first portion 99, the fluids travel down their independent channel sections and meet at the central section 90A of channel 90. In the central section 90A, all of the flow is laminar. The fluids travel down their respective sides of the central section 90A until they reach the outlet channel segments 90B, 90C. Surprisingly, the fluid that entered one inlet port 93 exits almost exclusively out of one exit channel 90C and exit port 95. The fluid that entered the other inlet port 92 exits out of the other channel segment 90B and exit port 94 almost exclusively. The only mixing that occurs in the central section 90A of channel 90 is through diffusional mixing at the relatively small lateral interface of the liquids. Because the width of these channels (about 60 mils) is much greater than their height (about 4 mils), the interfacial contact area between the two fluids is very small and the molecules at the interface must diffuse up to 30 mils in order for complete mixing to occur. At room temperature, diffusional motion is not sufficiently rapid for substantial mixing to occur in any reasonable period of time in the first functional portion 99.

The prior art-type 'side-by-side' microfluidic mixers can be improved slightly by lengthening the central channel, thereby extending the interfacial contact area between the two fluids, as in the next two functional regions 97, 98 shown in FIGS. 3A–3B. In these functional regions 97, 98, the length of the central channels 89A, 88A (where two fluids are in side-by-side interfactial contact) have been extended. However, very little mixing occurs even in these extended channels 89A, 88A. In addition, a slower flow-rate may be used to allow more time for the diffusion process to occur. However, this also results in incomplete mixing over any reasonable time period.

In contrast to the previous three functional regions 97–99, an overlap-type microfluidic mixer 96 is also provided in FIGS. 3A–3B. In this mixer 96, inlet channels 85, 87 were defined in different stencil sheets 81, 83. The inlet channels 85, 87 are in fluid communication at overlap region 102 where the two fluids to be mixed are forced to enter into an outlet channel 86, in this case defined in a stencil sheet 82 intermediate to the stencil sheets 81, 83 defining the two inlet channels 85, 87. In this mixer, at the overlap region 102 the interfacial contact area between the two fluids extends all the way across the width of the outlet channel 86 and is fifteen times greater than in the previous three functional areas 97–99. In addition, the average distance that the molecules need to diffuse in order for mixing to occur is now 2 mils, rather than 30 mils as in the previous functional areas 97–99.

A comparison of the mixing provided by the four functional regions 96–99 of the device 75 was demonstrated by performing a simple acid-base reaction within each region 96–99. In the overlap mixer 96, a 0.1M NaOH solution was injected (through an inlet port 77 and through-holes 106, 91) into one inlet channel 85, and a 0.5M HCl solution injected into the other inlet channel 87 (by way of another inlet port 76). The NaOH solution contained a small amount of bromo-phenol blue indicator (which is purple in basic solution, and yellow in acidic solution). Upon entering the overlap (mixing) region 102 of the mixer 96, the clear HCl solution and dark-purple NaOH solution mixed and reacted completely as evidenced by the color change of the indicator to a deep golden color (i.e., the stronger acidic solution neutralized the weaker basic solution, and the resulting mixture was weakly acidic). The reaction was also performed with a 0.1M HCl solution mixing with a 0.2M NaOH solution, in which the indicator was first dissolved in the acidic solution. In this experiment, the clear NaOH solution and yellow HCl solution mixed to create a dark purple fluid (in this case, the weaker acid is neutralized by the stronger base, resulting in a mixture that is weakly basic).

In comparison, a 'side-by-side' microfluidic mixer 99 according to a prior art design was also tested using these same solutions. In this mixer 99, little or no mixing occurred at the interface of the two liquids. The solutions that came out of the outlets 94, 95 on either side were the same color and pH as the solutions that were inputted at the corresponding inlet side.

The two fluids were then injected into the overlap-type microfluidic mixer 96. Again, a clear NaOH solution was supplied to one inlet port 76 and a yellow HCl solution (containing indicator) at the other inlet port 77. The two fluids begin to mix at the overlap region 102 and the mixing is nearly complete just after this overlap region 102 in the outlet channel 86. Dark fluid color was observed within the outlet channel 86 and at the outlet ports 78, 79, which was indicative of the acid-base reaction going to completion.

The difference in mixing behavior between the overlap-type and side-by-side mixers was also demonstrated by injecting water that had been dyed yellow into one inlet port 93 and blue-dyed fluid into another inlet port 92 of the side-by-side mixer 99. As the fluid flowed through the microfluidic channels 90A–90C of this 'mixer' 99, no mixing occurred. Referring to FIG. 4A, depicting the side-by-side mixer 99 of FIGS. 3A–3B in operation, yellow fluid 93A is injected into one inlet port 93 and blue fluid 92A into another inlet port 92. Note that no mixing occurs in the length of the channels 90A–90C. Referring to FIG. 4B, depicting another side-by-side mixer 97 of FIGS. 3A–3B in operation, yellow fluid 104A and blue fluid 105A are supplied to a snaking channel 88A; still no mixing occurred. Finally, referring to FIG. 4C, depicting the overlap-type mixer 96 of FIGS. 3A–3B in operation, yellow fluid 77A and blue fluid 76A are supplied to the mixer 96. The two fluids begin to mix at the overlap region 102 and the mixing is complete just after this overlap region 102 in the outlet channel 86 and all of the fluid in the outlet channel 86 is uniformly green.

More than two fluids can also be mixed with in an overlap-type microfluidic mixing device according to the present invention. Referring to FIGS. 5A–5B, a microfluidic mixing device 115 that receives and mixes three different fluids is shown. As illustrated in FIG. 5A, the device 115 is constructed with seven sheets of material 120–126, including upper and lower cover sheets 126, 120, stencil sheets 121, 123, 125, and spacer sheets 122, 124. The stencil sheets 121, 123, 125 define three inlet channels 127–129 and one outlet channel 136, which is a continuous extension of the inlet channel 128 defined in the central stencil sheet 123. Two inlet channels 127, 129 each have a widened end 127A, 129A. Each spacer sheet 122, 124 defines one wide aperture 130, 131, with the position of the apertures 130, 131 corresponding to the transition between the inlet channel 128 and the outlet channel 136 in the central stencil sheet 123. All of the channels 127–129, 136 have a nominal width of about sixty mils, and the apertures 130, 131 and widened ends 127A, 129A are about one hundred mils wide. The upper cover sheet 126 defines three fluidic inlet ports 133A–133C and one fluidic outlet port 134. Numerous through-holes 132, 137B–137C, 138B–138C, 139A–139B (each about eighty mils in diameter) are defined in four of the sheets 122–125. The six uppermost sheets 121–126 are all constructed from single sided tape (3 mil thick polypropylene backing with water based adhesive). The lower cover sheet 120 is constructed with 0.25 inch thick acrylic material. The assembled device 115 is shown in FIG. 5B.

In use, three different fluids are injected at the inlet ports 133A–133C. Each fluid travels through its respective inlet channel 127–129 until the fluids meet at the overlap junction 135. One fluid flows downward through the upper aperture 131 into the overlap junction, and another fluid flows upward through the lower aperture 130 into the overlap junction. Immediately downstream of the junction 135, the fluid from one inlet channel 129 is forced into the upper third of outlet channel 136, the fluid from another inlet channel 128 occupies the middle third of the outlet channel 136, and the fluid from the remaining inlet channel 127 occupies the bottom third of the outlet channel 136. Again, the interfacial contact area between the upper fluid and the middle fluid, and between the middle fluid and the lower fluid, is maximized in the outlet channel area 136. This causes very rapid diffusional mixing, so that the fluid exiting the device through the outlet port 134 is fully mixed. This mixing device 115 also allows for a tremendous range in mixing ratios. The flow rates of each of the fluids can be adjusted to allow a greater or lesser amount of each fluid to be added to the mixture.

As noted previously, for optimal performance of an overlap mixer, it is desirable to ensure that the fluids are laminated in stacked horizontal layers across the entire width of the outlet channel. For example, as an improvement to the mixer 15 illustrated in FIGS. 1A–1B, FIGS. 2A–2B illustrated three different mixers 71–73 having various mixer geometries that are more tolerant of minor fabrication faults such as slight misalignment of the stencil sheets with which the devices are composed. The mixer 115 illustrated in FIGS. 5A–5B also represents a fault-tolerant design, owing to both the presence of widened ends 127A, 129A at the inlet channels 127, 129, and to the presence of aperture-defining spacer sheets 122, 124 between inlet channels 127, 129 and the outlet channel 136. The use of aperture-defining spacer sheets can accommodate various placements of channels defined in adjacent sheets. It is particularly preferred for apertures defined in spacer sheets to be wider than the outlet channel of a mixer, to accommodate slight lateral misalignment of channels while still supplying input fluid across the entire width of the outlet channel.

Mixing may also be affected by varying the dimensions and/or geometry of an aperture defined in a spacer sheet. It is believed that a "short" aperture (that is, small in dimension from front to back in the direction of fluid flow) also helps impede fluid flow through the aperture, thus causing the fluid to be distributed across the entire width of the aperture before flowing through it—which helps to consistently ensure that the fluid is distributed across the entire width of the outlet channel to avoid "streaking" problems. FIGS. 6A–6B illustrate an overlap-type microfluidic mixing device 200 including a spacer sheet 203 defining an aperture 211 shaped as a short but wide slit. The device 200 may be fabricated with five sheets including upper and lower cover sheets 201, 205, two channel-defining stencil sheets 202, 204, and the aperture-defining spacer sheet. The upper cover sheet 201 defines one fluidic inlet port 206, and the lower cover sheet 205 defines one inlet port 207 and one outlet port 217. Through-holes 215, 216 aligned With the outlet port 217 are defined in the spacer sheet 203 and stencil sheet 204, respectively. One stencil sheet 202 defines an inlet channel 208 and an outlet channel 214 that is a continuous extension of the inlet channel 208, with the positioning of the slit 211 defining the transition from the inlet channel 208 to the outlet channel 214. The other stencil sheet 204 defines another inlet channel 210 having a widened end 210A. Preferably, as is the case in the device 200, at least a portion of the first inlet channel 208 immediately upstream of the overlap region 212, at least a portion of the second inlet channel 210 immediately upstream of the overlap region 212, and at least a portion of the outlet channel 214 immediately downstream of the overlap region 212 are substantially parallel to promote lamination of the first fluid and the second fluid in stacked horizontal layers across the entire width of the outlet channel 212.

In operation, a first fluid is supplied to one inlet channel 208 through one inlet port 206, and a second fluid is supplied to the other inlet channel 210 through the other inlet port 207. Upon reaching the widened end 210A of the inlet channel 204, flow of the second fluid is impeded slightly by the aperture or slit 211 defined in the spacer sheet 203. Preferably, to serve as an impedance, the aperture 211 should have a flow area (namely, cross-sectional area substantially perpendicular to the direction of fluid flow therethrough) that is smaller than the flow area of the corresponding (upstream) inlet channel 210. The aperture 211 is oriented with its width being parallel to the width of the outlet channel 214. Preferably, the aperture 211 has a width much greater than the adjacent outlet channel 214, and the aperture 211 is much shorter in front-to-back dimension (in the direction of approaching fluid flow) than in the width dimension. Preferable means of forming the aperture 211 include, for example, cutting through the spacer sheet 203 with a cutting blade (i.e., by merely separating but not removing material), or by using a laser cutter to remove a narrow line of material through the spacer sheet 203. It is believed that this impedance causes the approaching fluid to be distributed across the entire width of the aperture 211 before flowing through it. One fluid stream flows through the aperture 211 at an overlap region 212 to join the other fluid stream, and both fluids continue into the outlet channel 214. Because the aperture 211 is wider than the outlet channel 214, this helps ensure complete lamination of the two fluids in stacked horizontal layers across the entire width of the outlet channel 214 for optimal mixing. After flowing through the outlet channel 214, the resulting mixture flows through the through-holes 215–216 and exits the device 200 though the outlet port 217.

Figure 7B:
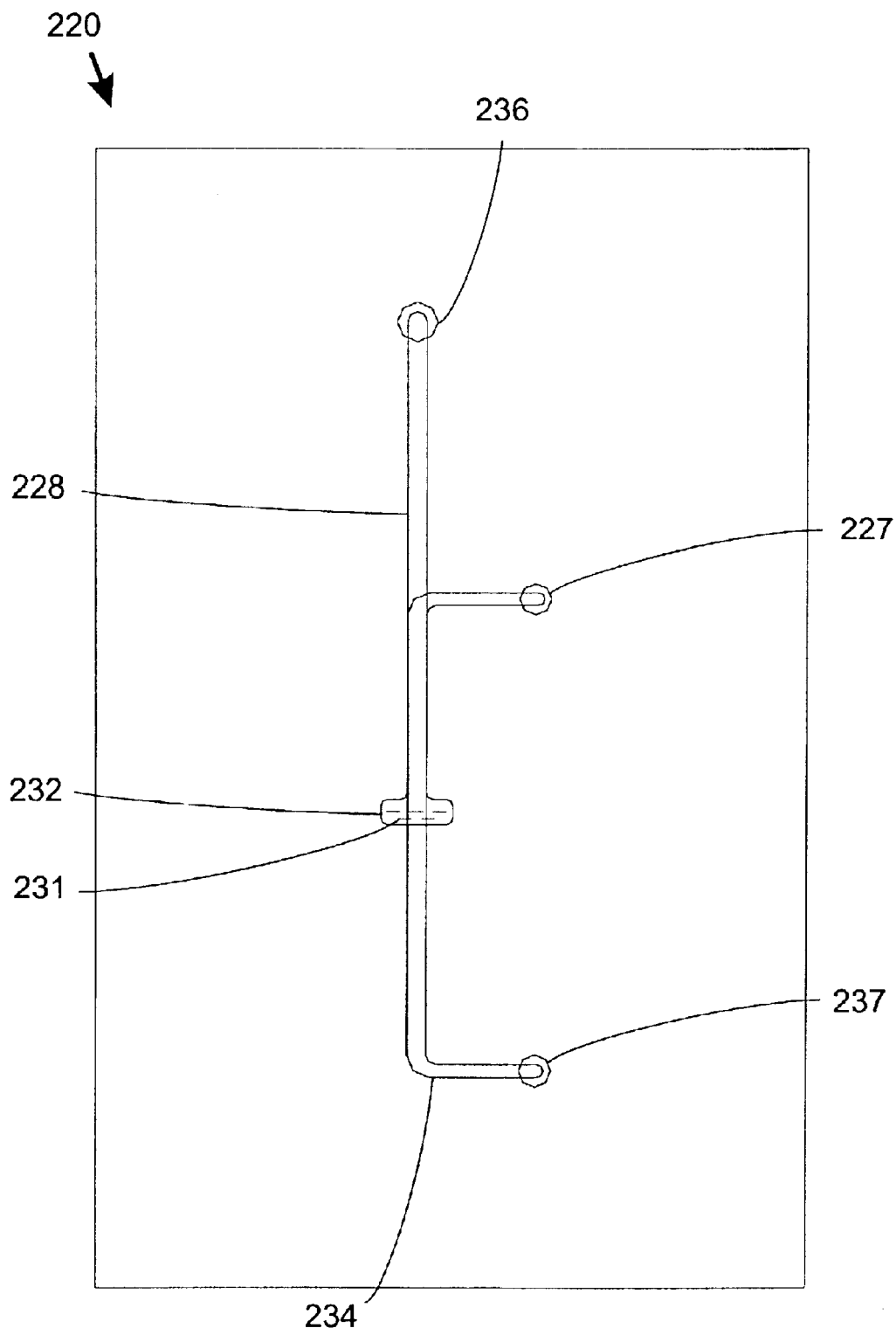
FIG. 7B is a top view of the assembled device of FIG. 7A.

In a variant of the design of the preceding device 200, similar functionality may be obtained by substituting multiple staggered apertures for the single wide aperture 211 defined in the spacer sheet 203 at the overlap region 212. For example, FIGS. 7A–7B illustrate a device 220 having, at the overlap region 232, several staggered apertures arranged in an uninterrupted fashion across the entire width of the outlet channel. In actuality, the aggregate width of the staggered apertures is greater than the width of the outlet channel to provide fault tolerance in case the adjacent stencil sheets are slightly misaligned during manufacture of the device 220. Briefly, the device 220 is fabricated with five sheets including upper and lower cover sheets 221, 225, two channel-defining stencil sheets 222, 224, and the aperture-defining spacer sheet. The upper cover sheet 221 defines one fluidic inlet port 226, and the lower cover sheet 225 defines one inlet port 227 and one outlet port 237. One stencil sheet 222 defines an inlet channel 228 and an outlet channel 234 that is a continuous extension of the inlet channel 208. The other stencil sheet 224 defines another inlet channel 230 having a widened end 230A. Through-holes 235, 236 aligned with the outlet port 237 are defined in the spacer sheet 223 and stencil sheet 224, respectively. Operation of the device 220 is substantially similar to operation of the preceding device 200, except that one fluid flows through the plurality of staggered apertures 231 rather than a single aperture 211.

Figure 8B:
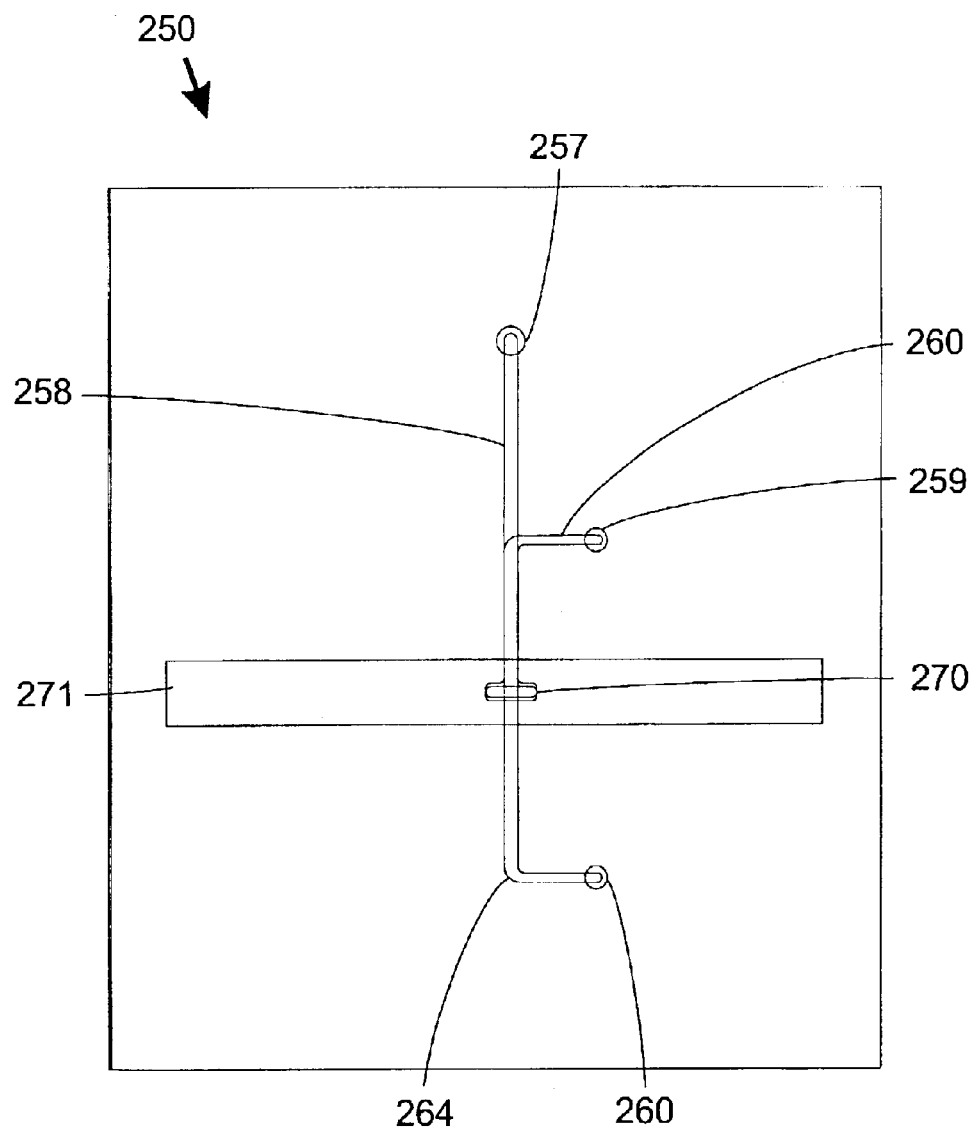
FIG. 8B is a top view of the assembled device of FIG. 8A.

Further embodiments utilize porous materials to aid in distributing a fluid across the entire width of an outlet channel to reduce streaking problems and thereby promote reliable mixing. For example, FIGS. 8A–8B illustrate an overlap-type microfluidic mixing device 250 that includes a porous material 271 disposed between two aperture-defining spacer sheets 253, 254. The device 250 is fabricated with six sheets 251–256, including upper and lower cover sheets 251, 256, two stencil sheets 252, 255, and two aperture defining spacer sheets 253, 254. Starting from the bottom of the device 250, the lower cover sheet 256 defines two inlet ports 259, 268. The adjacent stencil sheet 255 defines a through-hole 267 and an inlet channel 260 having a widened end 260A. Each spacer sheet 253, 254 is identical; each defines a through-hole 265, 266 and a rectangular aperture 272, 274. A porous membrane 271 disposed between the two spacer sheets 253, 254 is more specifically located between the two rectangular apertures 272, 274. While the porous membrane 271 depicted in FIGS. 8A–8B is smaller than the surrounding sheets 251–256 to conserve material, porous membranes of various sizes may be used. Another stencil sheet 252 defines an inlet channel 264 and an outlet channel 258, with the outlet channel 258 being a continuous extension of the inlet channel 264. Each channel 258, 260, 264 has a nominal width of about thirty mils (about 750 microns). The upper cover sheet 251 defines one fluidic outlet port 257.

Preferably, the sheets 251–256 comprise polyolefin materials such as 7.5-mil (188 micron) thickness "Clear Tear Seal" polypropylene (American Profol, Cedar Rapids, Iowa), and the porous membrane 271 comprises a permeable polyolefin material such as, for example, 1-mil thickness Celgard 2500 polypropylene membrane (55% porosity, 0.209×0.054 micron pore size, Celgard Inc., Charlotte, N.C.). The sheets 251–256 and porous membrane 271 are preferably bonded using an adhesiveless bonding method as described previously herein. Using such adhesiveless bonding methods with 7.5 mil thickness polypropylene material and channels about thirty mils wide, Applicants typically observe some shrinkage in the height of the channels— typical channels that result from the bonding process are between about 5 to 6 mils high. One advantage of using such an adhesiveless bonding method is that membrane 271 may be integrally bonded to the surrounding spacer sheets 253, 254 so as to prevent undesirable lateral wicking or leakage into the membrane 271 outside of the area immediately adjacent to the apertures 272, 274. A further advantage of using such an adhesiveless bonding method is that the resulting device 250 is capable of withstanding elevated pressures, typically up to several hundred p.s.i.

In operation, a first fluid is supplied to one inlet channel 260 (by way of an inlet port 259) and a second fluid is supplied to the other inlet channel 264 (by way of the other inlet port 268 and through-holes 265–267). The first fluid travels into the widened end 260A of the first channel 260 and the aperture 274 defined in the lower spacer sheet 254 adjacent to the porous membrane 271. The porous membrane 271 has a substantially smaller flow area than the corresponding inlet channel 260, and presents a significant impedance to fluid flow. As a result, the first fluid fills the entire aperture 274 as sufficient pressure builds to overcome the impedance of the membrane 271. When the fluid finally overcomes the impedance of the membrane 271, the fluid flows through the membrane 271 and through the aperture 272 defined in the other spacer sheet 253 to join the first fluid in the outlet channel 258 at an overlap region 270. Because the apertures 272, 274 are wider than the outlet channel 258, and the impedance provided by the porous membrane 271 forces the first fluid to fill the entire width of the apertures 272, 274, the first fluid is distributed across the entire width of the outlet channel 258. This distribution of the first fluid across the entire width of the outlet channel 258 helps to ensure reliable mixing by avoiding "streaking" problems. Just downstream of the overlap region 270, the two fluids are laminated one on top of the other in stacked horizontal layers in the outlet channel 258. Since the outlet channel 258 has a width of about thirty mils and a height between about 5 to 6 mils, the ratio of channel width to channel height is between about 5:1 and 6:1, with a resulting average diffusion path length of about 2.5 to 3 mils. Mixing occurs rapidly in the outlet channel 258, such that the resulting combination of fluids exiting the device 250 through the outlet port 257 is typically fully mixed.

In a variant of the design of the preceding device 200, a mixing device may including multiple porous membranes. For example, FIG. 9 illustrates a microfluidic mixing device 300 constructed with nine sheets of material (two cover sheets 301, 309, three stencil sheets 302, 305, 308, and four aperture-defining spacer sheets 303, 304, 306, 308) and two porous membranes 315, 325. Starting with the top of the device 300, the upper cover sheet 301 defines one fluidic inlet port 311 and one fluidic outlet port 334. The adjoining stencil sheet 302 defines a through-hole 333 and an inlet channel 312 having a widened end 312A. The upper two spacer sheets 303, 304 are identical; each defines a rectangular aperture 313, 314 and a through-hole 332, 331, respectively. The central stencil sheet 305 defines an outlet channel 330. The lower two spacer sheets 306, 307 are identical, each defining a rectangular aperture 324, 323, respectively. The lower stencil sheet 308 defines an inlet channel 322 having a widened end 322A. The lower cover sheet 309 defines one fluidic inlet port 320. One porous membrane 315 is disposed between the upper two cover sheets 303, 304, specifically positioned between the apertures 313, 314 defined in the cover sheets 303, 304. Another porous membrane 325 is disposed between the lower two cover sheets 307, 308 and positioned between the apertures 324, 323 defined in those cover sheets 307, 308. Preferably, the same materials are used to fabricate the device 300 as the preceding device 250 illustrated in FIGS. 8A–8B. When assembled, from top view the present device 300 looks identical to the device 250 illustrated in FIG. 8B.

In operation, a first fluid is supplied to one inlet channel 312 (by way of an inlet port 311) and a second fluid is supplied to the other inlet channel 322 (by way of the other inlet port 320). The first fluid travels into the widened end 312A of the first inlet channel 311 and into the aperture 313 defined in the upper spacer sheet 303. Because the porous membrane 315 presents a significant impedance to fluid flow, the first fluid fills the entire aperture 313 as sufficient pressure builds to overcome the impedance of the membrane 315. When the fluid finally overcomes the impedance of the membrane 315, the fluid flows through the adjoining aperture 314 into the outlet channel 330. Similarly, the second fluid travels into the widened end 322A of the second inlet channel 322 and into the aperture 323 defined in the lower spacer sheet 307. Due to the impedance presented by the lower porous membrane 325, the second fluid fills the entire aperture 323 as sufficient pressure builds to overcome the impedance of the membrane 325. When the second fluid finally overcomes the impedance of the lower membrane 325, the fluid flows through the adjoining aperture 324 and into the outlet channel 330 to join the first fluid. Because the apertures 313, 314, 323, 324 are wider than the outlet channel 330, and the impedance provided by the porous membranes 315, 325 forces the two fluids to fill the entire width of the respective apertures 313, 314, 323, 324, both the first fluid and the second fluid are distributed across the entire width of the outlet channel 258. This distribution helps ensure reliable mixing by avoiding "streaking" problems. Immediately downstream of the overlap region (in this case co-located with the apertures 314, 324), the first fluid and the second fluid are laminated in stacked horizontal layers across the entire width of the outlet channel 330, which promotes rapid mixing between the two fluids. At the end of the outlet channel 330, the combined fluids flow through three through-holes 331–333 and the outlet port 334 to exit the device 300.

It is also to be appreciated that the foregoing description of the invention has been presented for purposes of illustration and explanation, and is not intended to limit the invention to the precise manner of practice herein. It is to be appreciated, therefore, that various modifications of the invention in addition to those specifically shown and described herein will become apparent to those skilled in the art from review of the foregoing description. The scope of the invention, which is intended to encompass such modifications, should be interpreted with respect to the following claims and their equivalents.

What is claimed is:

1. A microfluidic device comprising:
    a plurality of stacked, substantially planar sheets of material including a first stencil sheet, a second stencil sheet, a spacer sheet disposed between the first stencil sheet and the second stencil sheet, an upper cover sheet, and a lower cover sheet, each sheet having an upper surface, an opposing lower surface, at least one edge, and a thickness, wherein each sheet of the plurality of sheets is joined to at least one other adjacent sheet such that the plane of the joint is substantially parallel to the upper and lower surfaces of each sheet;
    a first microfluidic inlet channel for supplying a first fluid, the first inlet channel being defined through the entire thickness of the first stencil sheet;
    a second microfluidic inlet channel for supplying a second fluid, the second inlet channel being defined through the entire thickness of the second stencil sheet; and
    a microfluidic outlet channel disposed downstream of the first inlet channel and the second inlet channel, the outlet channel having a width;
    wherein the spacer sheet defines an aperture having a width greater than the width of the outlet channel; and
    wherein at least a portion of the first inlet channel overlaps at least a portion of the second inlet channel at the aperture, thus permitting fluid communication between the first inlet channel, the second inlet channel, and the outlet channel.

2. The device of claim 1 wherein the outlet channel is a substantially continuous extension of the second inlet channel and is defined through the entire thickness of the second stencil sheet.

3. The device of claim 1, further comprising a third stencil sheet, wherein the outlet channel is defined through the entire thickness of the third stencil sheet.

4. The device of claim 3, wherein the third stencil sheet is disposed between the first stencil sheet and the second stencil sheet.

5. The device of claim 1 wherein at least one of the first inlet channel and the second inlet channel has a widened end adjacent to the aperture.

6. The device of claim 1 wherein at least one sheet of the plurality of sheets comprises a polymeric material.

7. The device of claim 1 wherein at least one sheet of the plurality of sheets comprises a polymeric material and is adhesivelessly joined to at least one other adjacent sheet.

8. The device of claim 1 wherein at least one sheet of the plurality of sheets is joined to at least one other adjacent sheet with an adhesive.

9. The device of claim 1 wherein at least one sheet of the plurality of sheets comprises a self-adhesive tape material having a carrier layer and an adhesive layer.

10. The device of claim 1 wherein at least one of the upper cover sheet and the lower cover sheet defines a first fluid inlet port in fluid communication with the first inlet channel and a second fluid inlet port in fluid communication with the second inlet channel.

11. The device of claim 1 wherein the first stencil sheet comprises a first material, the spacer sheet comprises a second material, and the first material is different from the second material.

\* \* \* \* \*